United States Patent
Totani et al.

(10) Patent No.: US 12,207,873 B2
(45) Date of Patent: Jan. 28, 2025

(54) OPTICAL COHERENCE TOMOGRAPHIC DEVICE

(71) Applicant: Tomey Corporation, Nagoya (JP)

(72) Inventors: Kota Totani, Nagoya (JP); Satoshi Sugiyama, Nagoya (JP)

(73) Assignee: Tomey Corporation, Nagoya (JP)

( * ) Notice: Subject to any disclaimer, the term of this patent is extended or adjusted under 35 U.S.C. 154(b) by 546 days.

(21) Appl. No.: 17/547,598

(22) Filed: Dec. 10, 2021

(65) Prior Publication Data

US 2022/0183552 A1 Jun. 16, 2022

(30) Foreign Application Priority Data

Dec. 14, 2020 (JP) ................. 2020-206907

(51) Int. Cl.
*A61B 3/10* (2006.01)
*A61B 3/00* (2006.01)
*A61B 3/14* (2006.01)

(52) U.S. Cl.
CPC ............ *A61B 3/102* (2013.01); *A61B 3/0033* (2013.01); *A61B 3/14* (2013.01)

(58) Field of Classification Search
CPC ......... A61B 3/102; A61B 3/0033; A61B 3/14; A61B 3/0025
USPC ....................................................... 351/206
See application file for complete search history.

(56) References Cited

U.S. PATENT DOCUMENTS

| | | |
|---|---|---|
| 2012/0121158 A1 | 5/2012 | Sekine et al. |
| 2012/0249769 A1 | 10/2012 | Naba et al. |
| 2014/0078466 A1 | 3/2014 | Sekine et al. |
| 2016/0198951 A1 | 7/2016 | Fujino et al. |
| 2017/0228521 A1 | 8/2017 | Appakaya et al. |
| 2018/0064331 A1 | 3/2018 | Naba et al. |

FOREIGN PATENT DOCUMENTS

| | | |
|---|---|---|
| JP | 2011-024930 A | 2/2011 |
| JP | 2012-213602 A | 11/2012 |

*Primary Examiner* — Tuyen Tra
*Assistant Examiner* — Rahman Abdur
(74) *Attorney, Agent, or Firm* — Shumaker, Loop & Kendrick, LLP

(57) ABSTRACT

An optical coherence tomographic device may include: an image capturing unit configured to capture a tomographic image of a subject eye; an input device configured to input one or a plurality of examination report types, each of the examination report types indicating an intended examination report form; a memory configured to store a plurality of control programs, each of the plurality of control programs, for corresponding one of the examination report types, is used for causing the image capturing unit to perform capturing for generating an examination report of the corresponding type; and a controller configured to control the image capturing unit, when the plurality of examination report types is inputted, according to a series of control programs generated based on corresponding ones of control programs stored in the memory.

4 Claims, 10 Drawing Sheets

FIG. 6

| Examination Report | Capturing Step | Setting Details ||||||||||
| --- | --- | --- | --- | --- | --- | --- | --- | --- | --- | --- |
| | | Scan Method | B-Scan Range | C-Scan Range | Scan Direction | A/B Scan | B/C Scan | Slice Repeat | Fixation | Focus |
| Polarization Map | Cube | Cube | 6.0 | 6.0 | 0 | 512 | 128 | 1 | Macula | Retina |
| Macula Map | Cube | Cube | 6.0 | 6.0 | 0 | 512 | 128 | 1 | Macula | Retina |
| Glaucoma Map | Cube | Cube | 6.0 | 6.0 | 0 | 512 | 128 | 1 | Macula | Retina |
| | Cube Disc | Cube | 6.0 | 6.0 | 0 | 512 | 128 | 1 | Disc | Retina |
| Optic Disc Shape Analysis | Cube Disc | Cube | 6.0 | 6.0 | 0 | 512 | 128 | 1 | Disc | Retina |
| | Circle Disc | Circle | 3.45 | - | TSNIT | 512 | 1 | 30 | Disc | Retina |

OPTICAL COHERENCE TOMOGRAPHIC DEVICE

CROSS REFERENCE

The present application claims priority to Japanese Patent Application No. 2020-206907, filed on Dec. 14, 2020, the entire contents of which are incorporated herein by reference.

TECHNICAL FIELD

The technology disclosed herein relates to an optical coherence tomographic device.

BACKGROUND

An optical coherence tomographic device for obtaining a tomographic image of a subject eye has been developed. The optical coherence tomographic device includes a measurement optical system for inputting light from a light source to the subject eye and guiding light reflected from the subject eye, and a reference optical system for inputting the light from the light source to a reference surface and guiding light reflected from the reference surface. In measurement of the subject eye, the tomographic image of the subject eye is generated from interference light generated by combining the reflected light (measurement light) guided by the measurement optical system and the reflected light (reference light) guided by the reference optical system. In such an optical coherence tomographic image device, in order to obtain captured image including intended examination form, it is necessary to set capturing conditions such as a scan pattern at the time of capturing, as necessary. For example, in an optical coherence tomographic device disclosed in Japanese Patent Application Publication No. 2011-24930, capturing conditions (i.e., operation mode) corresponding to an examination type are set in advance. An examiner selects the operation mode suitable for an intended examination. Then, the optical coherence tomographic device captures a subject eye in accordance with the capturing conditions corresponding to the selected operation mode, analyzes results of the capturing, and outputs an examination report form of the examination corresponding to the selected operation mode. Therefore, when the examiner selects the operation mode, the examiner obtains the examination report form in accordance with the selected operation mode without setting detailed capturing conditions.

SUMMARY

In the optical coherence tomographic device described in Japanese Patent Application Publication No. 2011-24930, when the examiner selects the operation mode, the capturing is performed under the capturing conditions corresponding to the selected operation mode, and a report in an examination report form corresponding to the selected operation mode is generated. That is, in the optical coherence tomographic device of Japanese Patent Application Publication No. 2011-24930, the operation mode is associated with the corresponding capturing conditions and the corresponding examination report. Therefore, when examinations of a plurality of examination types are to be performed on the subject eye, capturing is first performed under capturing conditions corresponding to one operation mode, and thereafter, capturing is performed under capturing conditions corresponding to a next operation mode different from the previous operation mode. Therefore, when a plurality of types of examinations is performed, it is necessary to repeat operations for capturing as many times as the number of examination types, and burden on an examinee and burden on an examiner are increased by repeating the capturing many times.

The disclosure herein discloses a technique for reducing burden on an examinee and an examiner in performing examinations of a plurality of examination types.

A first optical coherence tomographic device disclosed herein may comprise: an image capturing unit configured to capture a tomographic image of a subject eye; an input device configured to input one or a plurality of examination report types, each of the examination report types indicating an intended examination result report form; a memory configured to store a plurality of control programs, each of the plurality of control programs, for corresponding one of the examination report types, is used for causing the image capturing unit to perform capturing for generating an examination report of the corresponding type; and a controller configured to control the image capturing unit, when the plurality of examination report types is inputted, according to a series of control programs generated based on corresponding ones of control programs stored in the memory.

A second coherence tomographic device disclosed herein may comprise: an image capturing unit configured to capture a tomographic image of a subject eye; a memory configured to store a control program for causing the image capturing unit to perform capturing from which examination reports of a plurality of examination report types are able to be generated; a controller configured to cause the image capturing unit to perform the capturing according to the control program stored in the memory; an input device configured to input at least one type of the plurality of examination report types; and a generator configured to generate at least one of the examination reports corresponding to the at least one type inputted by the input device based on specific capturing data comprised in a group of captured data obtained by the controller causing the image capturing unit to perform the capturing according to the control program.

BRIEF DESCRIPTION OF DRAWINGS

FIG. 6 is a diagram illustrating an example of details of examination report types and corresponding capturing step(s) and settings.

DETAILED DESCRIPTION

Figure 1:
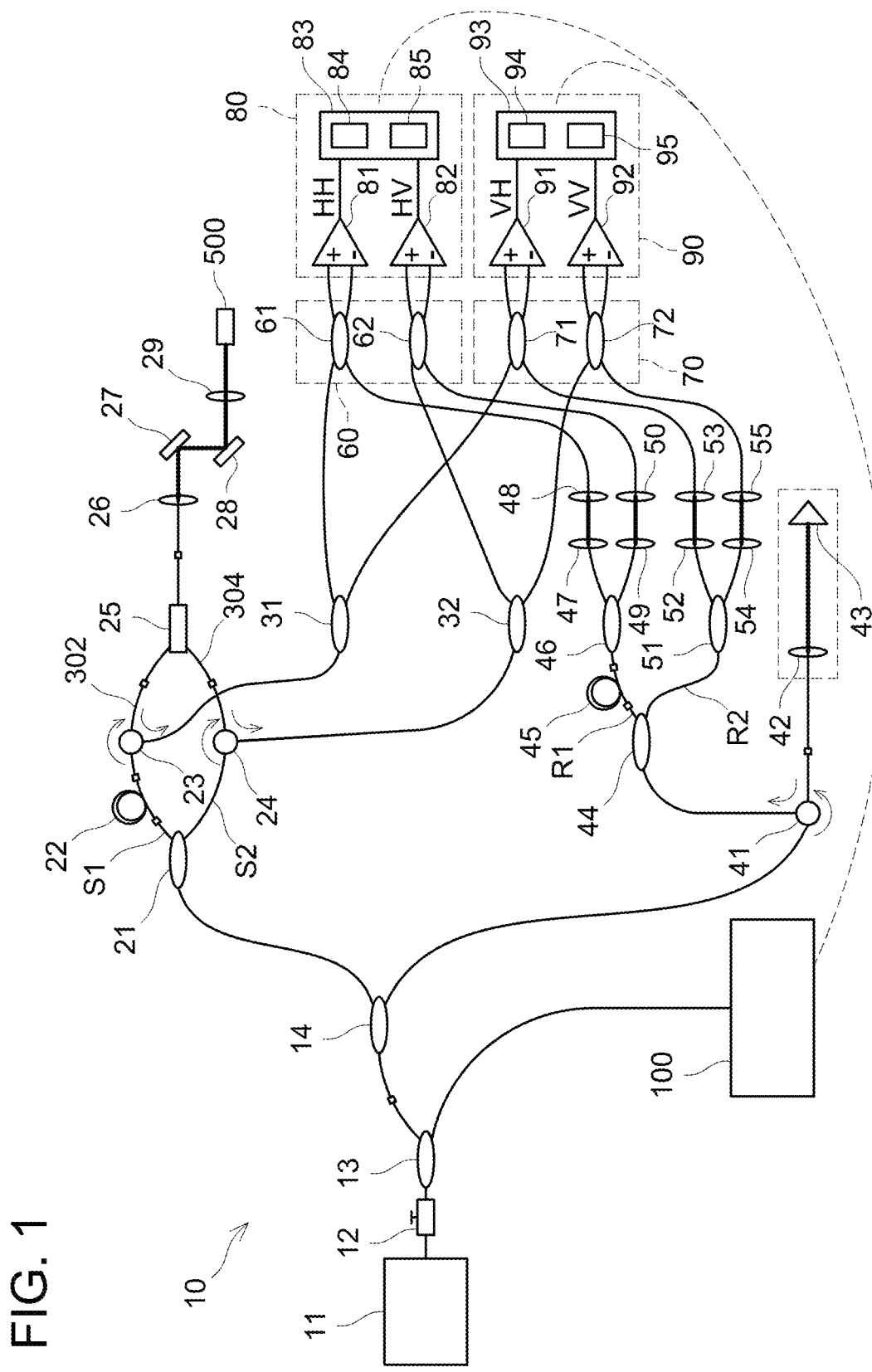
FIG. 1 illustrates a schematic configuration of an optical system of an optical coherence tomographic device according to first and second embodiments.

Representative, non-limiting examples of the present disclosure will now be described in further detail with reference to the attached drawings. This detailed description is merely intended to teach a person of skill in the art further details for practicing preferred aspects of the present teachings and is not intended to limit the scope of the present disclosure. Furthermore, each of the additional features and teachings disclosed below may be utilized separately or in conjunction with other features and teachings to provide improved optical coherence tomographic devices, as well as methods for using and manufacturing the same.

Moreover, combinations of features and steps disclosed in the following detailed description may not be necessary to practice the present disclosure in the broadest sense, and are instead taught merely to particularly describe representative examples of the present disclosure. Furthermore, various features of the above-described and below-described representative examples, as well as the various independent and dependent claims, may be combined in ways that are not specifically and explicitly enumerated in order to provide additional useful embodiments of the present teachings.

All features disclosed in the description and/or the claims are intended to be disclosed separately and independently from each other for the purpose of original written disclosure, as well as for the purpose of restricting the claimed subject matter, independent of the compositions of the features in the embodiments and/or the claims. In addition, all value ranges or indications of groups of entities are intended to disclose every possible intermediate value or intermediate entity for the purpose of original written disclosure, as well as for the purpose of restricting the claimed subject matter.

Some of the features characteristic to below-described embodiments will herein be listed. It should be noted that the respective technical elements are independent of one another, and are useful solely or in combinations. The combinations thereof are not limited to those described in the claims as originally filed.

A first optical coherence tomographic device disclosed herein may comprise: an image capturing unit configured to capture a tomographic image of a subject eye; an input device configured to input one or a plurality of examination report types, each of the examination report types indicating a desired an intended examination result report form; a memory configured to store a plurality of control programs, each of the plurality of control programs, for corresponding one of the examination report types, is used for causing the image capturing unit to perform capturing for generating an examination report of the corresponding type; and a controller configured to control the image capturing unit, when the plurality of examination report types is inputted, according to a series of control programs generated based on corresponding ones of control programs stored in the memory.

In the above-described optical coherence tomographic device, when the plurality of examination report types is inputted, the series of control programs is generated based on the control programs corresponding to the plurality of examination report types that are inputted. Since the image capturing unit is controlled according to the series of control programs, the capturing is performed at once by the series of control programs even when examination reports of the plurality of examination report types are to be generated. Therefore, it is unnecessary to separately perform operations for capturing as many times as the number of examination report types to be generated, and burden on an examinee and burden on an examiner can be reduced.

In the optical coherence tomographic device disclosed herein, the examination report type may comprise a first examination report type indicating a first examination report form and a second examination report type indicating a second examination report form. A first control program corresponding to the first examination report type may include a specific capturing step. A second control program corresponding to the second examination report type may include the specific capturing step. When the first examination report type and the second examination report type are inputted by the input device, the controller may be configured to generate the series of control programs by omitting the specific capturing step comprised in one of the first control program and the second control program. According to such a configuration, when the first examination report and the second examination report are to be generated, it is possible to omit performing the specific capturing step included (overlapping) in both the first examination report and the second examination report. Therefore, a time required for capturing to generate the first examination report and the second examination report can be reduced, and burden on the examinee can be reduced.

In the optical coherence tomographic device disclosed herein, for each of the examination report types, the controller may be configured to generate an examination report of the examination report type based on captured data captured by performing a capturing step corresponding to the examination report type among a group of captured data obtained by performing the series of control programs. According to such a configuration, the examination report is generated by using the captured data appropriate for corresponding one of the examination report types among the group of captured data obtained by performing the series of control programs. For example, the group of captured data obtained by performing the series of control programs may include captured data unnecessary for generating a certain examination report as well as captured data necessary for generating the examination report. By using the captured data appropriate for each of the examination report types, the corresponding examination report can be appropriately generated.

The optical coherence tomographic device disclosed herein may further comprise an output device configured to output examination reports of the plurality of examination report types generated from captured data captured according to the series of control programs. According to such a configuration, the examiner can obtain the examination reports of the plurality of examination report types and grasp results of the examination.

A second coherence tomographic device disclosed herein may comprise: an image capturing unit configured to capture a tomographic image of a subject eye; a memory configured to store a control program for causing the image capturing unit to perform capturing from which examination reports of a plurality of examination report types are able to be generated; a controller configured to cause the image capturing unit to perform the capturing according to the control program stored in the memory; an input device configured to input at least one type of the plurality of examination report types; and a generator configured to generate at least one of the examination reports corresponding to the at least one type inputted by the input device based on specific capturing data comprised in a group of captured data obtained by the controller causing the image capturing unit to perform the capturing according to the control program.

In the above optical coherence tomographic device, the controller is configured to cause the image capturing unit to perform the capturing according to the control program for causing the image capturing unit to execute one capturing from which the examination reports of the plurality of examination report types are able to be generated. Therefore, whichever examination report type(s) is selected among the plurality of examination report types, the generator can generate corresponding one(s) of the examination reports of the plurality of examination report types. For example, even if it is determined that different examination report(s) is necessary after specific examination report(s) is checked, it is unnecessary to perform capturing for generating the different examination report(s). Therefore, it is unnecessary to repeat capturing operations many times, and burden on the examinee and burden on the examiner can be reduced.

EMBODIMENTS

First Embodiment

Hereinafter, an optical coherence tomographic device according to the present embodiment will be described. The optical coherence tomographic device according to the present embodiment is a polarization-sensitive OCT (PS-OCT) that is capable of capturing polarization characteristics of a subject to be examined by a Fourier domain method of a wavelength sweeping type using a light source of a wavelength sweeping type (swept-source optical coherence tomography: SS-OCT).

As illustrated in FIG. 1, the optical coherence tomographic device according to the present embodiment comprises a light source 11; a measurement optical system (21 to 29, 31, 32) that generates a measurement light from light outputted from the light source 11; a reference optical system (41 to 46, 51) that generates reference light from the light outputted from the light source 11; interference optical systems 60, 70 that combine reflected light from a subject eye 500 generated in the measurement optical system with the reference light generated in the reference optical system to generate interference light; and interference light detectors 80, 90 that detect the interference light generated in the interference optical system 60, 70.

(Light Source)

The light source 11 is a light source of a wavelength sweeping type, and the wavelength (wavenumber) of output light varies with a predetermined cycle. Since the wavelength of light with which the subject eye 500 is irradiated varies (sweeps), an intensity distribution of light reflected from depthwise portions of the subject eye 500 can be obtained by subjecting a signal obtained from interference light, which is a combination of the reflected light from the subject eye 500 and the reference light, to Fourier analysis.

A polarization control device 12 and a fiber coupler 13 are connected to the light source 11, and a PMFC (polarization maintaining fiber coupler) 14 and a sampling trigger/clock generator 100 are connected to the fiber coupler 13. Therefore, the light outputted from the light source 11 is inputted to the PMFC 14 and the sampling trigger/clock generator 100 through the polarization control device 12 and the fiber coupler 13. The sampling trigger/clock generator 100 generates a sampling trigger and a sampling clock for each of signal processors 83 and 93 (which will be described later) by using the light from the light source 11.

(Measurement Optical System)

The measurement optical system (21 to 29, 31, 32) comprises a PMFC 21 connected to the PMFC 14; two measurement light paths S1 and S2 branching off from the PMFC 21; a polarization beam combiner/splitter 25 connecting the two measurement light paths S1 and S2; a collimator lens 26 connected to the polarization beam combiner/splitter 25; galvanometer mirrors 27 and 28; and a lens 29. An optical path length difference generator 22 and a circulator 23 are disposed on the measurement light path S1. Only a circulator 24 is disposed on the measurement light path S2. Therefore, an optical path length difference ΔL between the measurement light path S1 and the measurement light path S2 is generated by the optical path length difference generator 22. The optical path length difference ΔL may be set to be longer than a depthwise measurement range of the subject eye 500. This prevents interference light with different optical path lengths from overlapping each other. As the optical path length difference generator 22, for example, an optical fiber may be used or an optical system such as a mirror, a prism, etc. may be used. In the present embodiment, a PM fiber with a length of one meter is used as the optical path length difference generator 22. The measurement optical system further comprises PMFCs 31, 32. The PMFC 31 is connected to the circulator 23. The PMFC 32 is connected to the circulator 24.

One of light (i.e., measurement light) split by the PMFC 14 is inputted to the measurement optical system (21 to 29, 31, 32). The PMFC 21 splits the measurement light inputted from the PMFC 14 into first measurement light and second measurement light. The first measurement light split by the PMFC 21 is guided to the measurement light path S1, and the second measurement light split by the PMFC 21 is guided to the measurement light path S2. The first measurement light guided to the measurement light path S1 is inputted to the polarization beam combiner/splitter 25 through the optical path length difference generator 22 and the circulator 23. The second measurement light guided to the measurement light path S2 is inputted to the polarization beam combiner/splitter 25 through the circulator 24. A PM fiber 304 is connected to the polarization beam combiner/splitter 25 such that the PM fiber 304 is circumferentially turned by 90 degrees relative to a PM fiber 302. For this reason, the second measurement light inputted to the polarization beam combiner/splitter 25 has a polarization component orthogonal to the first measurement light. Since the optical path length difference generator 22 is disposed on the measurement light path S1, the first measurement light is delayed relative to the second measurement light by a distance corresponding to the optical path length difference generator 22 (that is, the optical path length difference ΔL is generated). The polarization beam combiner/splitter 25 superimposes the inputted first measurement light and second measurement light. The light outputted from the polarization beam combiner/splitter 25 (superimposed light of the first measurement light and the second measurement light) passes through the collimator lens 26, the galvanometer mirrors 27 and 28, and the lens 29 and is then inputted to the subject eye 500. The light inputted to the subject eye 500 is scanned along an x-y direction by the galvanometer minors 27 and 28.

The light inputted to the subject eye 500 is reflected by the subject eye 500. The reflected light by the subject eye 500 scatters at the surface of the subject eye 500 and the inside thereof. The reflected light from the subject eye 500 passes through, in the reverse order to the incidence path, the lens 29, the galvanometer mirrors 28, 27, and the collimator lens 26, and is then inputted to the polarization beam combiner/splitter 25. The polarization beam combiner/splitter 25 splits the inputted reflected light into two polarization components that are orthogonal to each other. These are termed horizontal polarization reflected light (horizontal polarization component) and vertical polarization reflected light (vertical polarization component), for convenience sake. The horizontal polarization reflected light is guided to the measurement light path S1, and the vertical polarization reflected light is guided to the measurement light path S2.

The optical path of the horizontal polarization reflected light is changed by the circulator 23, and the horizontal polarization reflected light is inputted to the PMFC 31. The PMFC 31 splits the inputted horizontal polarization reflected light so that it is inputted to each of PMFCs 61, 71. Therefore, the horizontal polarization reflected light inputted to each of the PMFCs 61, 71 contains a reflected light component based on the first measurement light and a reflected light component based on the second measurement light. The optical path of the vertical polarization reflected light is changed by the circulator 24, and the vertical polarization reflected light is inputted to the PMFC 32. The PMFC 32 splits the inputted vertical polarization reflected light so that it is inputted to each of PMFCs 62, 72. Therefore, the vertical polarization reflected light inputted to each of the PMFCs 62, 72 contains a reflected light component based on the first measurement light and a reflected light component based on the second measurement light.

(Reference Optical System)

The reference optical system (41 to 46, 51) comprises a circulator 41 connected to the PMFC 14; a reference delay line (42, 43) connected to the circulator 41; a PMFC 44 connected to the circulator 41; two reference light paths R1 and R2 branching off from the PMFC 44; a PMFC 46 connected to the reference light path R1; and a PMFC 51 connected to the reference light path R2. An optical path length difference generator 45 is disposed on the reference light path R1. No optical path length difference generator is disposed on the reference light path R2. Therefore, an optical path length difference $\Delta L'$ between the reference light path R1 and the reference light path R2 is generated by the optical path length difference generator 45. For example, an optical fiber is used as the optical path length difference generator 45. The optical path length difference $\Delta L'$ of the optical path length difference generator 45 may be the same as the optical path length difference $\Delta L$ of the optical path length difference generator 22. If the optical path length differences $\Delta L$ and $\Delta L'$ are the same, depthwise positions of a plurality of interference light (described later) in the subject eye 500 coincide with each other. That is, it is unnecessary to align a plurality of acquired tomographic images.

The other of light split by the PMFC 14 (i.e., reference light) is inputted to the reference optical system (41 to 46, 51). The reference light inputted from the PMFC 14 is inputted to the reference delay line (42, 43) through the circulator 41. The reference delay line (42, 43) includes a collimator lens 42 and a reference mirror 43. The reference light inputted to the reference delay line (42, 43) is inputted to the reference mirror 43 through the collimator lens 42. The reference light reflected by the reference mirror 43 is inputted to the circulator 41 through the collimator lens 42. The reference mirror 43 is movable in directions to approach and separate from the collimator lens 42. In the present embodiment, the position of the reference mirror 43 is adjusted before the start of measurement so that a signal from the subject eye 500 will be within an OCT depthwise measurable range.

The optical path of the reference light reflected by the reference mirror 43 is changed by the circulator 41, and the reference light reflected by the reference mirror 43 is inputted to the PMFC 44. The PMFC 44 splits the inputted reference light into first reference light and second reference light. The first reference light is guided to the reference light path R1, and the second reference light is guided to the reference light path R2. The first reference light is inputted to the PMFC 46 through the optical path length difference generator 45. The reference light inputted to the PMFC 46 is split into first split reference light and second split reference light. The first split reference light is inputted to the PMFC 61 through a collimator lens 47 and a lens 48. The second split reference light is inputted to the PMFC 62 through a collimator lens 49 and a lens 50. The second reference light is inputted to the PMFC 51 and then is split into third split reference light and fourth split reference light. The third split reference light is inputted to the PMFC 71 through a collimator lens 52 and a lens 53. The fourth split reference light is inputted to the PMFC 72 through a collimator lens 54 and a lens 55.

(Interference Optical System)

The interference optical systems 60, 70 include a first interference optical system 60 and a second interference optical system 70. The first interference optical system 60 includes the PMFCs 61 and 62. As described, the horizontal polarization reflected light from the measurement optical system and the first split reference light (light having the optical path length difference $\Delta L'$) from the reference optical system are inputted to the PMFC 61. Here, the horizontal polarization reflected light contains a reflected light component (light having the optical path length difference $\Delta L$) based on the first measurement light and a reflected light component (light that does not have the optical path length difference $\Delta L$) based on the second measurement light. Therefore, in the PMFC 61, the first split reference light is combined with the reflected light component (light having the optical path length difference $\Delta L$) based on the first measurement light which is among the horizontal polarization reflected light, as a result of which first interference light (horizontal polarization component) is generated.

The vertical polarization reflected light from the measurement optical system and the second split reference light (light having the optical path length difference $\Delta L'$) from the reference optical system are inputted to the PMFC 62. Here, the vertical polarization reflected light contains a reflected light component (light having the optical path length difference $\Delta L$) based on the first measurement light and a reflected light component (light that does not have the optical path length difference $\Delta L$) based on the second measurement light. Therefore, in the PMFC 62, the second split reference light is combined with the reflected light component (light having the optical path length difference $\Delta L$) based on the first measurement light which is among the vertical polarization reflected light, as a result of which second interference light (vertical polarization component) is generated.

The second interference optical system 70 includes the PMFCs 71 and 72. As described, the horizontal polarization reflected light from the measurement optical system and the third split reference light (light that does not have the optical path length difference $\Delta L'$) from the reference optical system are inputted to the PMFC 71. Therefore, in the PMFC 71, the third split reference light is combined with a reflected light component (light that does not have the optical path length difference ΔL) based on the second measurement light which is among the horizontal polarization reflected light, as a result of which third interference light (horizontal polarization component) is generated.

The vertical polarization reflected light from the measurement optical system and the fourth split reference light (light that does not have the optical path length difference ΔL') from the reference optical system are inputted to the PMFC 72. Therefore, in the PMFC 72, the fourth split reference light is combined with the reflected light component (light that does not have the optical path length difference ΔL) based on the second measurement light which is among the vertical polarization reflected light, as a result of which fourth interference light (vertical polarization component) is generated. The first interference light and the second interference light correspond to the measurement light that has passed through the measurement light path S1, and the third interference light and the fourth interference light correspond to the measurement light that has passed through the measurement light path S2.

(Interference Light Detectors)

The interference light detectors 80, 90 include a first interference light detector 80 configured to detect the interference light (the first interference light and the second interference light) generated in the first interference light generator 60, and a second interference light detector 90 configured to detect the interference light (the third interference light and the fourth interference light) generated in the second interference light generator 70.

The first interference light detector 80 comprises balanced light detectors 81 and 82 (which may simply be termed detectors 81, 82 hereinbelow), and a signal processor 83 connected to the detectors 81 and 82. The PMFC 61 is connected to the detector 81, and the signal processor 83 is connected to an output terminal of the detector 81. The PMFC 61 splits the first interference light into two interference light that have phases different from each other by 180 degrees, and inputs the two interference light to the detector 81. The detector 81 performs differential amplification processing and noise reduction processing to the two interference light having phases different from each other by 180 degrees inputted from the PMFC 61 so as to convert them to an electric signal (first interference signal), and outputs the first interference signal to the signal processor 83. That is, the first interference signal is an interference signal HH between the reference light and the horizontal polarization reflected light from the subject eye 500 based on the horizontal polarization measurement light. Similarly, the PMFC 62 is connected to the detector 82, and the signal processor 83 is connected to an output terminal of the detector 82. The PMFC 62 splits the second interference light into two interference light that have phases different from each other by 180 degrees, and inputs the two interference light to the detector 82. The detector 82 performs differential amplification processing and noise reduction processing to the two interference light having phases different from each other by 180 degrees so as to convert them to an electric signal (second interference signal), and outputs the second interference signal to the signal processor 83. That is, the second interference signal is an interference signal HV between the reference light and the vertical polarization reflected light from the subject eye 500 based on the horizontal polarization measurement light.

The signal processor 83 comprises a first signal processing unit 84 to which the first interference signal is inputted, and a second signal processing unit 85 to which the second interference signal is inputted. The first signal processing unit 84 is configured to sample the first interference signal based on a sampling trigger and a sampling clock inputted to the signal processor 83 from the sampling trigger/clock generator 100. The second signal processing unit 85 is configured to sample the second interference signal based on the sampling trigger and the sampling clock inputted to the signal processor 83 from the sampling trigger/clock generator 100. The first and second interference signals sampled in the first signal processing unit 84 and the second signal processing unit 85 are inputted to a processor 202 (which will be described later). A known data acquisition device (a so-called DAQ) may be used as the signal processor 83.

Similar to the first interference light detector 80, the second interference light detector 90 comprises balanced light detectors 91 and 92 (which may simply be termed detectors 91, 92 hereinbelow), and the signal processor 93 connected to the detectors 91 and 92. The PMFC 71 is connected to the detector 91, and the signal processor 93 is connected to an output terminal of the detector 91. The PMFC 71 splits the third interference light into two interference light that have phases different from each other by 180 degrees, and inputs the two interference light to the detector 91. The detector 91 performs differential amplification processing and noise reduction processing to the two interference light having phases different from each other by 180 degrees so as to convert them to an electric signal (third interference signal), and outputs the third interference signal to the signal processor 93. That is, the third interference signal is an interference signal VH between the reference light and the horizontal polarization reflected light from the subject eye 500 based on the vertical polarization measurement light. Similarly, the PMFC 72 is connected to the detector 92, and the signal processor 93 is connected to an output terminal of the detector 92. The PMFC 72 splits the fourth interference light into two interference light that have phases different from each other by 180 degrees, and inputs the two interference light to the detector 92. The detector 92 performs differential amplification processing and noise reduction processing to the two interference light having phases different from each other by 180 degrees so as to convert them to an electric signal (fourth interference signal), and outputs the fourth interference signal to the signal processor 93. That is, the fourth interference signal is an interference signal VV between the reference light and the vertical polarization reflected light from the subject eye 500 based on the vertical polarization measurement light.

The signal processor 93 comprises a third signal processing unit 94 to which the third interference signal is inputted, and a fourth signal processing unit 95 to which the fourth interference signal is inputted. The third signal processing unit 94 is configured to sample the third interference signal based on a sampling trigger and a sampling clock inputted to the signal processor 93 from the sampling trigger/clock generator 100. The fourth signal processing unit 95 is configured to sample the fourth interference signal based on the sampling trigger and the sampling clock inputted to the signal processor 93 from the sampling trigger/clock generator 100. The third and fourth interference signals sampled in the third signal processing unit 94 and the fourth signal processing unit 95 are inputted to the processor 202 (which will be described later). A known data acquisition device (a so-called DAQ) may also be used as the signal processor 93. According to the above configuration, it is possible to acquire the interference signals indicative of four polarization characteristics of the subject eye 500. In the present embodiment, the signal processors 83, 93, each of which comprises two signal processing units, are used, however, different configurations may be employed. For example, one signal processor comprising four signal processing units may be used, or four signal processors each comprising one signal processing unit may be used.

Figure 2:
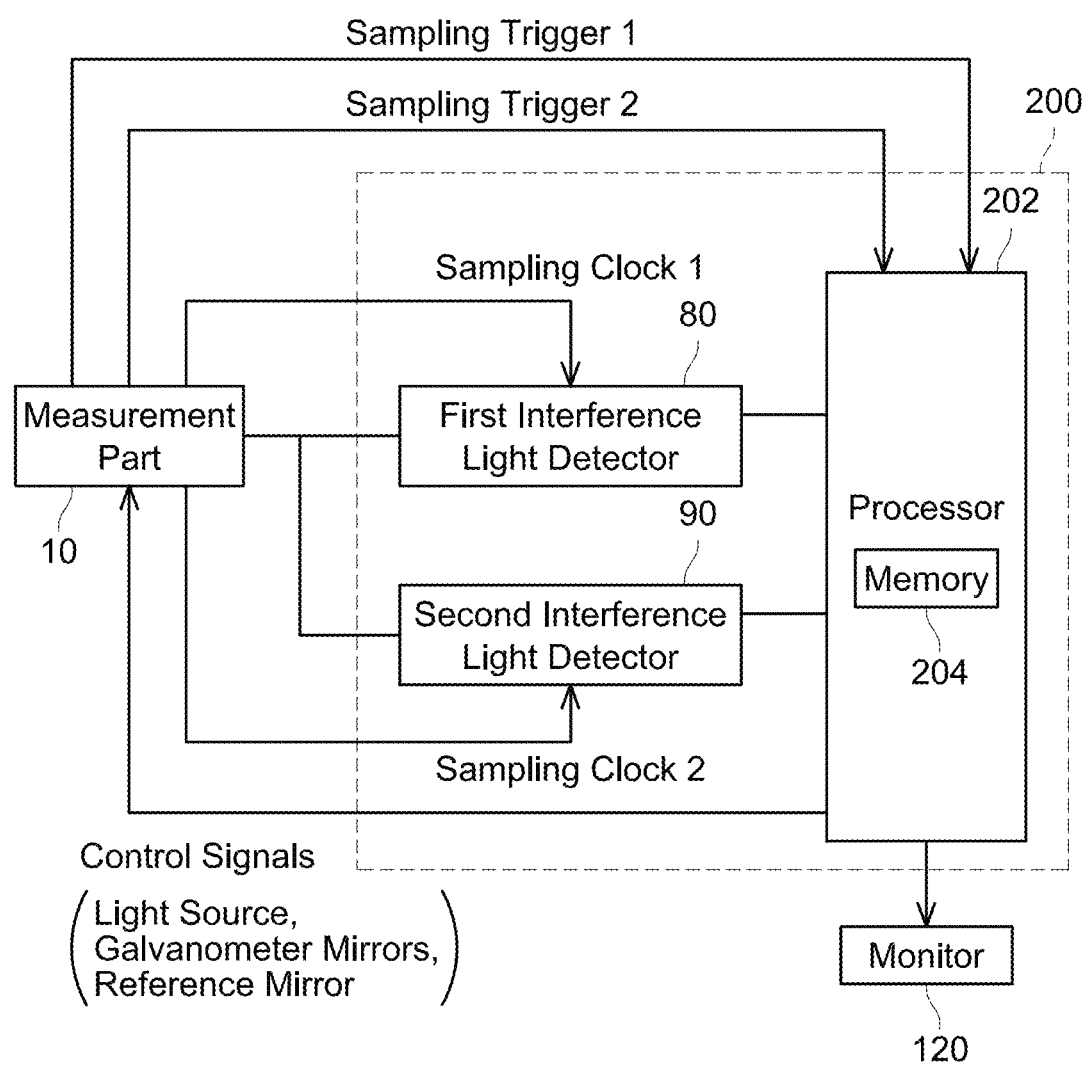
FIG. 2 is a block diagram illustrating a control system of the optical coherence tomographic device according to the first and second embodiments.

Next, the configuration of a control system of the optical coherence tomographic device according to the present embodiment will be described. As illustrated in FIG. 2, the optical coherence tomographic device is controlled by a calculation unit 200. The calculation unit 200 comprises the processor 202, the first interference light detector 80, and the second interference light detector 90. The first interference light detector 80, the second interference light detector 90, and the processor 202 are connected to a measurement unit 10. The processor 202 is configured to output a control signal to the measurement unit 10 to move an incidence position of the measurement light to the subject eye 500 by driving the galvanometer mirrors 27 and 28. The first interference light detector 80 acquires first sampling data with respect to the interference signals (the interference signal HH and the interference signal HV) inputted from the measurement unit 10 based on a sampling clock 1 inputted from the measurement unit 10 and by using a sampling trigger 1 as a trigger, and outputs the first sampling data to the processor 202. The processor 202 performs calculation processing such as Fourier transform, etc. to the first sampling data to generate an HH tomographic image and an HV tomographic image. The second interference light detector 90 acquires second sampling data with respect to the interference signals (the interference signal VH and the interference signal VV) inputted from the measurement unit 10 based on a sampling clock 2 inputted from the measurement unit 10 and by using a sampling trigger 2 as a trigger, and outputs the second sampling data to the processor 202. The processor 202 performs calculation processing such as Fourier transform, etc. to the second sampling data to generate a VH tomographic image and a VV tomographic image. The HH tomographic image, the VH tomographic image, the HV tomographic image, and the VV tomographic image are tomographic images at the same position. Thus, the processor 202 can create tomographic images with four polarization characteristics (HH, HV, VH, VV) that represent a Jones matrix of the subject eye 500.

The processor 202 includes a memory 204. The memory 204 stores a plurality of control programs, each of which is for generating an examination report indicating a result of an examination on the subject eye 500 in a specific examination report form and a plurality of control programs, each of which is for performing capturing in accordance with an examination report type corresponding to the examination report. Each of the control programs for generating the examination reports is stored in the memory 204 for corresponding one of the examination report types. Each of the control programs for performing capturing is stored in the memory 204 in association with the corresponding one of the examination report types for the corresponding one of the examination report types. Each of the control programs for performing capturing is constituted by one or more capturing steps, and the capturing step(s) necessary for generating the examination report corresponding to the control program is set in advance. More specifically, the memory 204 stores an examination report name and corresponding one of the control programs for preforming capturing in association with each other. These control programs may be set by the examiner. That is, the examiner may set specific capturing condition(s) for each of the capturing step(s) constituting corresponding one of the control programs, and associate the condition(s) with the corresponding examination report name to set the same as the control program. The control program set by the examiner can also be stored in the memory 204. Specific examples of the examination reports and the control programs for performing capturing including the capturing step(s) associated with examination reports will be described later.

Figure 3:
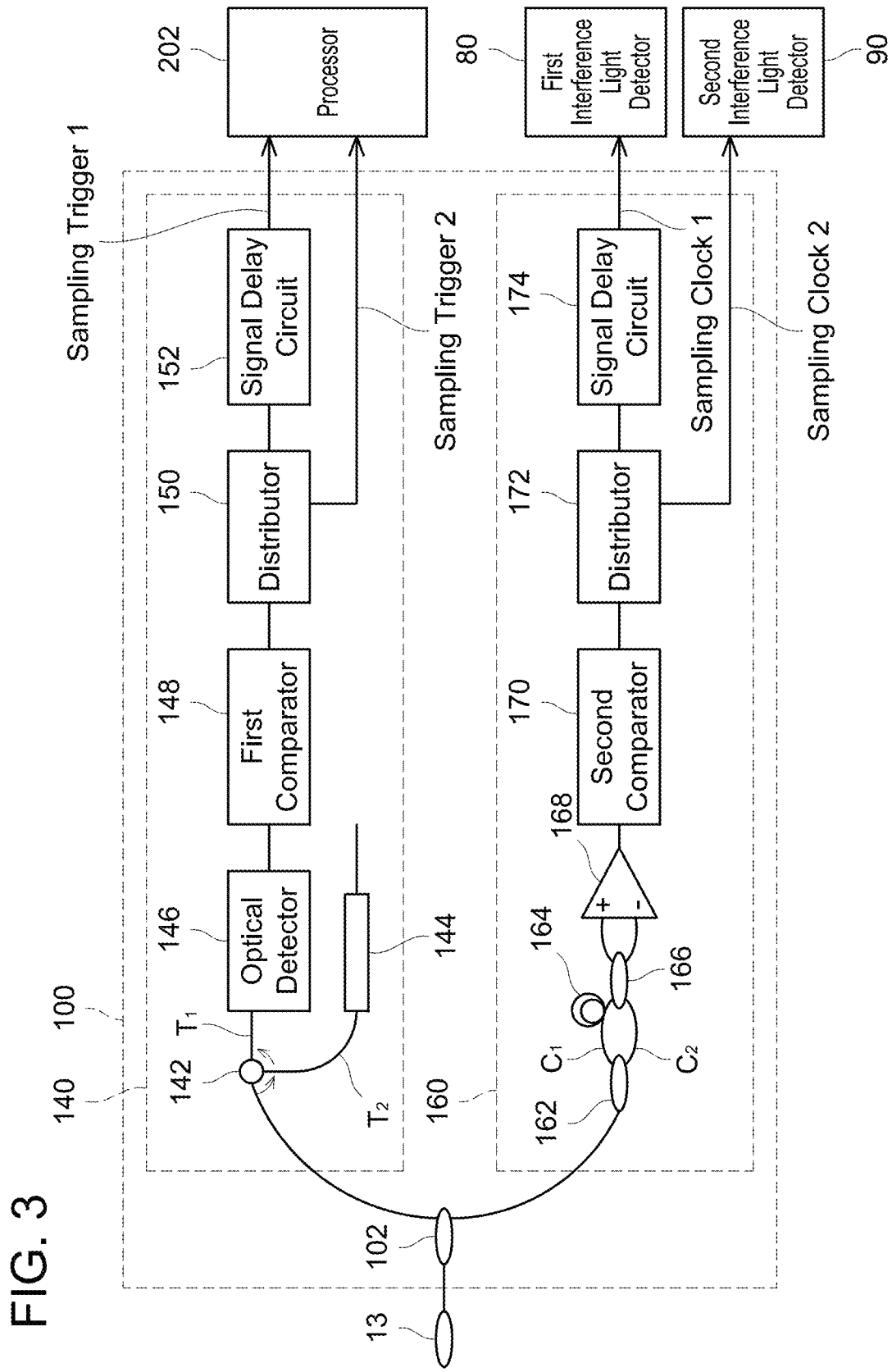
FIG. 3 is a block diagram illustrating a configuration of a sampling trigger/clock generator.

As illustrated in FIG. 3, the sampling trigger/clock generator 100 comprises a fiber coupler 102, a sampling trigger generator (140, 142, 144, 146, 148, 150, 152), and a sampling clock generator (160, 162, 164, 166, 168, 170, 172, 174). The light from the light source 11 is inputted, through the fiber coupler 13 and the fiber coupler 102, to each of the sampling trigger generator 140 and the sampling clock generator 160.

(Sampling Trigger Generator)

The sampling trigger generator 140 may generate a sampling trigger by using, for example, an FBG (fiber bragg grating) 144. As illustrated in FIG. 3, the FBG 144 reflects only a component of the light inputted from the light source 11 that has a specific wavelength, thereby generating a sampling trigger. The generated sampling trigger is inputted to a distributor 150. The distributor 150 distributes the sampling trigger into the sampling trigger 1 and the sampling trigger 2. The sampling trigger 1 is inputted, through a signal delay circuit 152, to the processor 202. The sampling trigger 2 is directly inputted to the processor 202. The sampling trigger 1 is a trigger signal for the interference signals (the first interference signal and the second interference signal) inputted from the first interference light detector 80 to the processor 202. The sampling trigger 2 is a trigger signal for the interference signals (the third interference signal and the fourth interference signal) inputted from the second interference light detector 90 to the processor 202. The signal delay circuit 152 is designed such that the sampling trigger 1 is delayed relative to the sampling trigger 2 by a time corresponding to the optical path length difference $\Delta L$ of the optical path length difference generator 22. This makes it possible to make a frequency at which the sampling of the interference signals inputted from the first interference light detector 80 is started equal to a frequency at which the sampling of the interference signals inputted from the second interference light detector 90 is started. Only the sampling trigger 1 may be generated. Since the optical path length difference $\Delta L$ is known, the sampling of the interference signals inputted from the second interference light detector 90 may be started such that the start time is delayed from the sampling trigger 1 by a time corresponding to the optical path length difference $\Delta L$.

(Sampling Clock Generator)

The sampling clock generator may be configured of a Mach-Zehnder interferometer, for example. As illustrated in FIG. 3, the sampling clock generator generates a sampling clock with the same frequency by using the Mach-Zehnder interferometer. The sampling clock generated by the Mach-Zehnder interferometer is inputted to a distributor 172. The distributor 172 distributes the sampling clock into the sampling clock 1 and the sampling clock 2. The sampling clock 1 is inputted, through a signal delay circuit 174, to the first interference light detector 80. The sampling clock 2 is directly inputted to the second interference light detector 90. The signal delay circuit 174 is designed to cause a delay by a time corresponding to the optical path length difference $\Delta L$ of the optical path length difference generator 22. This makes it possible to sample interference light with the delay corresponding to the optical path length difference generator 22 at the same timing Thus, positional misalignment among a plurality of acquired tomographic images can be prevented. In the present embodiment, a Mach-Zehnder interferometer is used to generate the sampling clocks. Alternatively, a Michelson interferometer or an electric circuit may be used to generate the sampling clocks. Alternatively, the sampling clocks may be generated by using a light source including a sampling clock generator.

Figure 4:
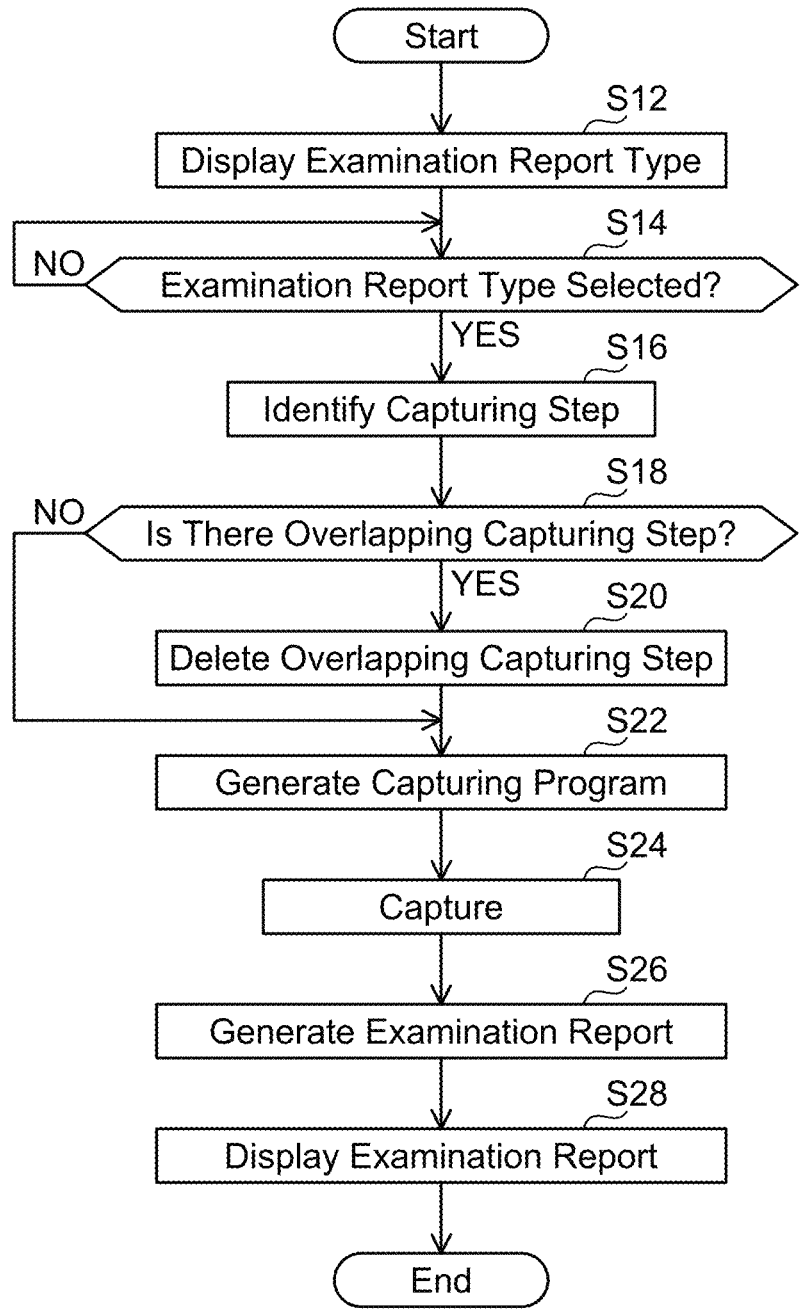
FIG. 4 is a flowchart illustrating an example of a process for generating examination report(s) in the first embodiment.

Next, with reference to FIG. 4, a process to generate examination report(s) of the subject eye 500 will be described. As illustrated in FIG. 4, first, the processor 202 displays examination report types that can be generated by the optical coherence tomographic device of the present embodiment on the monitor 120 (see FIG. 2) (S12). The memory 204 stores the examination report types that can be generated by the optical coherence tomographic device of the present embodiment. The processor 202 causes the monitor 120 to display all the examination report types that can be generated and are stored in the memory 204.

Figure 5:
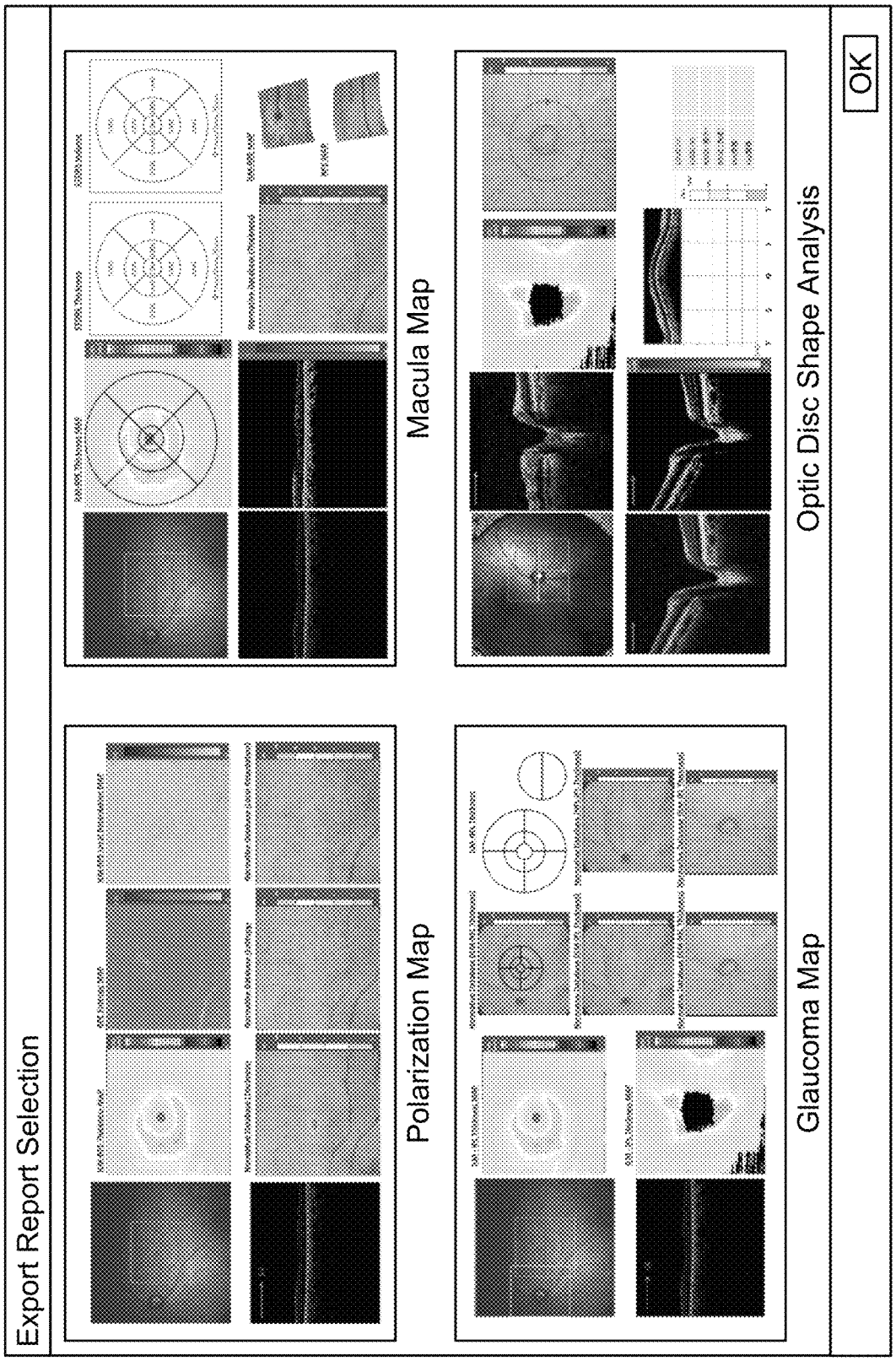
FIG. 5 is an image illustrating an example of a screen for selecting examination report(s).

For example, in the present embodiment, it is assumed that four examination reports of "Polarization Map", "Macula Map", "Glaucoma Map" and "Optic Disc Shape Analysis" can be generated. In this case, as illustrated in FIG. 5, the processor 202 causes the monitor 120 to display the four examination report types of the "Polarization Map", "Macula Map", "Glaucoma Map" and "Optic Disc Shape Analysis" in a selectable manner.

Next, the processor 202 determines whether one or a plurality of examination report types have been selected (S14). Specifically, the examiner selects one or a plurality of examination reports types each corresponding to an intended examination from the plurality of examination report types displayed on the monitor 120 by using an input means (not shown) such as a mouse. In the example illustrated in FIG. 5, the examiner selects one or a plurality of intended examination report types from the "Polarization Map", "Macula Map", "Glaucoma Map" and "Optic Disc Shape Analysis". Here, the number of examination report type(s) selected by the examiner is not particularly limited. Therefore, the examiner can select a plurality of intended examination report types. For example, the examiner selects three examination report types: the "Polarization Map", "Macula Map", and "Glaucoma Map". When an operation of selecting the one or plurality of examination report types is completed, the examiner instructs completion of the selection operation. For example, the examiner instructs the completion of the selection operation by pressing an "OK" button displayed on the monitor 120 using the input means. The processor 202 awaits until the completion of the selection operation is instructed (NO in step S14).

When the completion of the selection operation is instructed (YES in step S14), the processor 202 identifies capturing step(s) associated with each of the examination report types selected in step S14 (S16). As described above, the memory 204 stores the capturing step(s) necessary for generating each of the one or plurality of examination reports in association with the corresponding examination report type. The processor 202 reads out, from the memory 204, the capturing step(s) corresponding to each the one or plurality of examination report types selected in step S14.

For example, as illustrated in FIG. 6, the memory 204 stores a plurality of examination report types, corresponding capturing step(s) for each of the examination report types and detailed capturing conditions of the capturing step(s). In the example illustrated in FIG. 6, the capturing step of "Polarization Map" is "Cube". Accordingly, the processor 202 determines that the capturing step of the selected "Polarization Map" is "Cube." Similarly, the processor 202 determines that the capturing step of the selected "Macula Map" is "Cube", and determines that the capturing steps of the selected "Glaucoma Map" are "Cube" and "Cube Disk".

Next, in step S18, the processor 202 determines whether there is overlapping capturing step(s) among the capturing step(s) identified in step S16. When a plurality of examination report types is selected in step S14, there may be a case where capturing step(s) associated with the selected examination report types overlap one another (that is, the same capturing step(s) is included in the selected examination report types). For example, as illustrated in FIG. 6, when the "Polarization Map", "Macula Map" and "Glaucoma Map" are selected, the capturing step of "Cube" overlaps in all three examination report types. Therefore, when the three examination report types of the "Polarization Map", "Macula Map" and "Glaucoma Map" are selected in step S14, the processor 202 determines that the capturing step of "Cube" overlaps.

When there is overlapping capturing step(s) (YES in step S18), the processor 202 deletes the overlapping capturing step(s) (S20). For example, if three examination report types of the "Polarization Map", "Macula Map" and "Glaucoma Map" are selected in step S14, the capturing steps identified in step S16 are the "Cube" associated with the "Polarization Map", the "Cube" associated with the "Macula Map", and the "Cube" and "Cube Disk" associated with the "Glaucoma Map". Therefore, the list of all the capturing steps associated with the three selected examination report types is the "Cube", "Cube", "Cube" and "Cube Disk", thus there are three "Cube". In this instance, the processor 202 deletes the overlapping "Cube" (i.e., two of the three "Cube") from the listed four capturing steps. Then, the two capturing steps of "Cube" and "Cube Disk" are left. On the other hand, when there is no overlapping capturing step (NO in step S18), the processor 202 skips step S20.

Next, the processor 202 generates a series of control programs (hereinafter, also referred to as a capturing program) based on the capturing step(s) identified in Steps S16 to S20 (S22). If it is determined in step S18 that there is overlapping capturing step(s), the overlapping capturing step(s) is deleted in step S20. Therefore, the overlapping capturing step(s) is deleted from all the capturing steps identified in step S16, and the capturing program is generated for the remaining capturing step(s). For example, when three examination report types of the "Polarization Map", "Macula Map" and "Glaucoma Map" are selected in step S14, the two capturing steps of "Cube" and "Cube Disk" are left after step S20. Accordingly, the processor 202 generates the capturing program to perform the two capturing steps of the "Cube" and "Cube Disk". On the other hand, when it is determined that there is no overlapping capturing step in step S18, the processor 202 generates the capturing program so as to execute all the capturing step(s) identified in step S16.

Next, the processor 202 performs capturing of the subject eye 500 (S24) in accordance with the capturing program generated in step S22. The process of capturing the subject eye 500 is performed under the following procedure. First, the examiner manipulates a manipulation member such as a joystick (not shown) to align the optical coherence tomographic device with respect to the subject eye 500. That is, the processor 202 operates a position adjustment mechanism (not shown) in accordance with the examiner's manipulation of the manipulation member. As a result, a position of the optical coherence tomographic device in xy directions (vertical and horizontal directions) and a position of the optical coherence tomographic device in z directions (forward and backward directions) with respect to the subject eye 500 are adjusted. Thereafter, the processor 202 performs capturing of the subject eye 500 according to the capturing program. As described above, the capturing program consists of one or more capturing steps, and detailed setting conditions (capturing conditions) for each of the one or more capturing steps are stored in the memory 204. The processor 202 performs the capturing program in accordance with the detailed setting conditions stored in the memory 204. For example, when the three examination report types of the "Polarization Map", "Macula Map" and "Glaucoma Map" are selected in step S14, a capturing program consisting of the two capturing steps of the "Cube" and "Cube Disk" is generated. Consequently, the processor 202 performs the two capturing steps of the "Cube" and "Cube Disk" according to the capturing program. Captured data captured in each of the capturing step(s) is stored in the memory 204. In the following, a plurality of pieces of data captured in each of the capturing step(s) may be collectively referred to as "a group of captured data".

When the capturing of the subject eye 500 is completed, the processor 202 generates the examination report(s) of the examination report type(s) selected in step S14 (S26). In step S24, one or more capturing steps are performed, and the captured data captured in each of the one or more capturing steps is stored in the memory 204. The processor 202 generates each of the examination report(s) by using the captured data captured in the capturing step(s) corresponding to the examination report type(s) from the group of captured data.

For example, when the three examination report types of the "Polarization Map", "Macula Map" and "Glaucoma Map" are selected in step S14, the two capturing steps of the "Cube" and "Cube Disk" are performed. As illustrated in FIG. 6, the capturing step corresponding to the "Polarization Map" is the "Cube". Consequently, the processor 202 generates the "Polarization Map" by using the captured data captured in the "Cube". Since the capturing step corresponding to the "Macula Map" is the "Cube", the processor 202 also generates the "Macula Map" by using the captured data captured in the "Cube". Both the "Polarization Map" and the "Macula Map" can be generated by using the captured data captured in the "Cube", and each of the "Polarization Map" and the "Macula Map" can be generated by changing the analysis procedures, site(s) to be analyzed of the subject eye 500, and the like. In addition, since the captured steps corresponding to the "Glaucoma Map" are the "Cube" and the "Cube Disk", the captured data captured in the "Cube" is also used for generating the "Glaucoma Map". As described above, when a plurality of examination report types that can be generated by performing the same capturing step(s) is selected, captured data captured in the same capturing step(s) (in the present embodiment, the "Cube") can be used to generate any of the different examination reports once the same capturing step(s) is performed. In the present embodiment, when the capturing step(s) overlap, the overlapping capturing step(s) is deleted to generate the capturing program. Consequently, a time required for capturing can be reduced, and burden on an examinee can be reduced.

Even when there is no overlapping capturing step, after one or a plurality of examination report types are selected, the capturing program is generated by combining capturing step(s) so that all the selected examination report(s) can be generated. For example, in the example illustrated in FIG. 6, when two examination report types of the "Polarization Map" and "Optic Disc Shape Analysis" are selected, the "Cube" corresponding to the "Polarization Map", and the "Cube Disk" and the "Circle Disk" corresponding to the "Optic Disc Shape Analysis" are identified as the capturing steps. Consequently, the capturing program consisting of the three steps of the "Cube", "Cube Disk" and "Circle Disk" is generated. When this capturing program is performed, the three capturing steps of the "Cube", "Cube Disk" and "Circle Disk" are performed in a series of operations. As such, since capturing for generating a plurality of examination reports is executed at a time, it is not necessary to separately instruct and perform capturing for generating each of the examination reports, and it is possible to reduce a time required for capturing all the examination reports.

Lastly, the processor 202 displays the examination report(s) generated in step S26 on the monitor 120 (S28). When a plurality of examination report types is selected, all the examination reports may be displayed on a single screen, or each of the examination reports may be displayed such that the examination reports are switched from one to the other to display only one examination report on a single screen.

Figure 7:
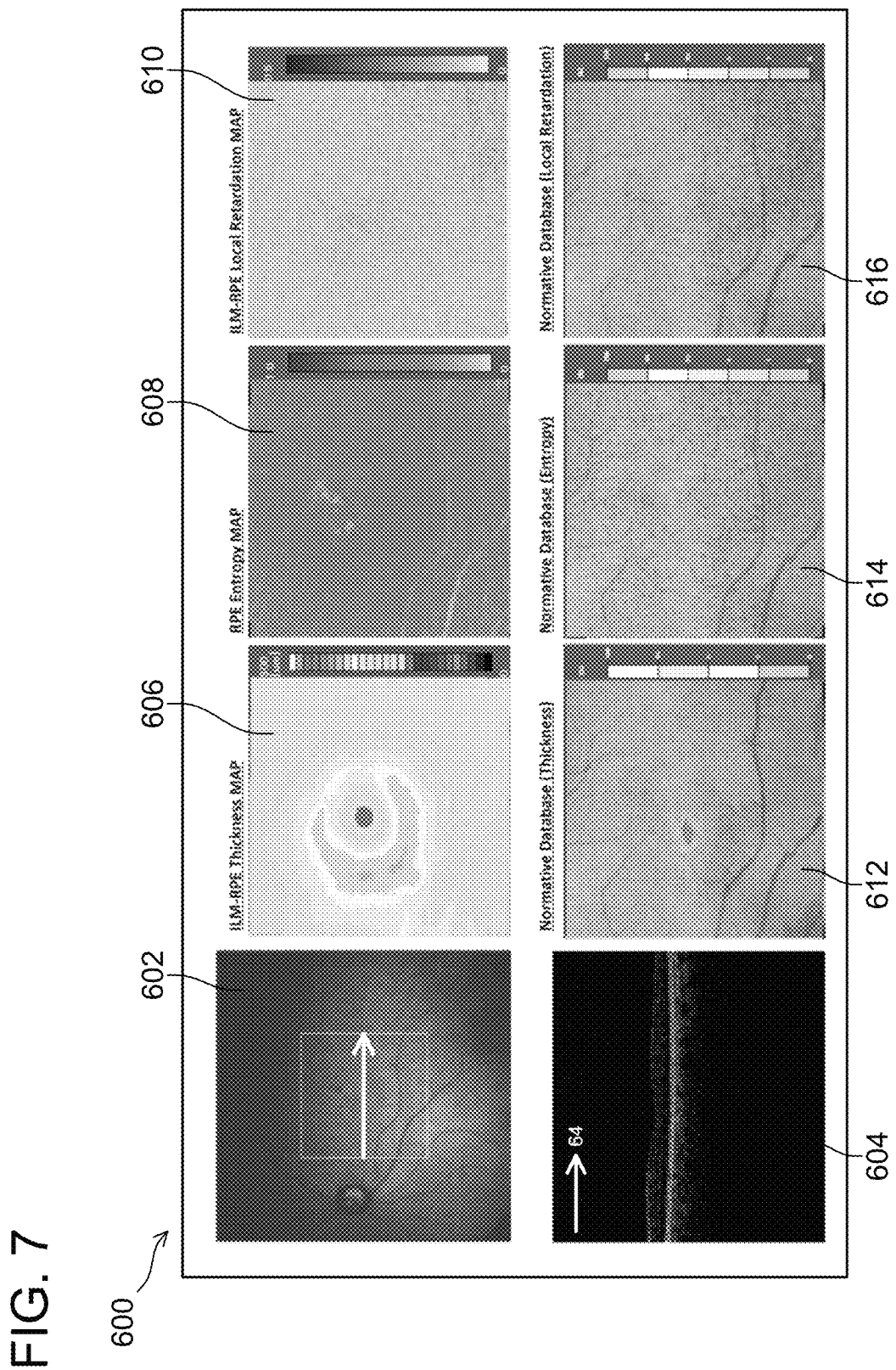
FIG. 7 illustrates an image indicating a polarization map which is an example of the examination report(s).

FIG. 7 is an example of display images 600 of the polarization map. The polarization map is generated by analyzing the captured data captured in the capturing step set as "Cube". As illustrated in FIG. 7, the polarization map includes a fundus image 602, a tomographic image 604, an en-face image 606 indicating thickness, an en-face image 608 indicating entropy, and an en-face image 610 indicating birefringence of the subject eye 500. The tomographic image 604 shows a cross section at a position indicated by the arrow in the fundus image 602. Each of the en-face images 606, 608, and 610 shows a region surrounded by the square in the fundus image 602. The polarization map also includes an en-face image 612 indicating thickness, an en-face image 614 indicating entropy, and an en-face image 616 indicating birefringence of an eye in a normal state (hereinafter, also referred to simply as a "normal eye") that differs from the subject eye 500. Since the polarization map includes the en-face images 612, 614, and 616 of the normal eye, the condition of the subject eye 500 can be easily grasped by comparing the subject eye 500 with the normal eye. As described above, by virtue of the polarization map including the images relating to various polarizations that can be generated from the captured data captured in the "Cube", it becomes easier to grasp the state of the subject eye 500.

Figure 8:
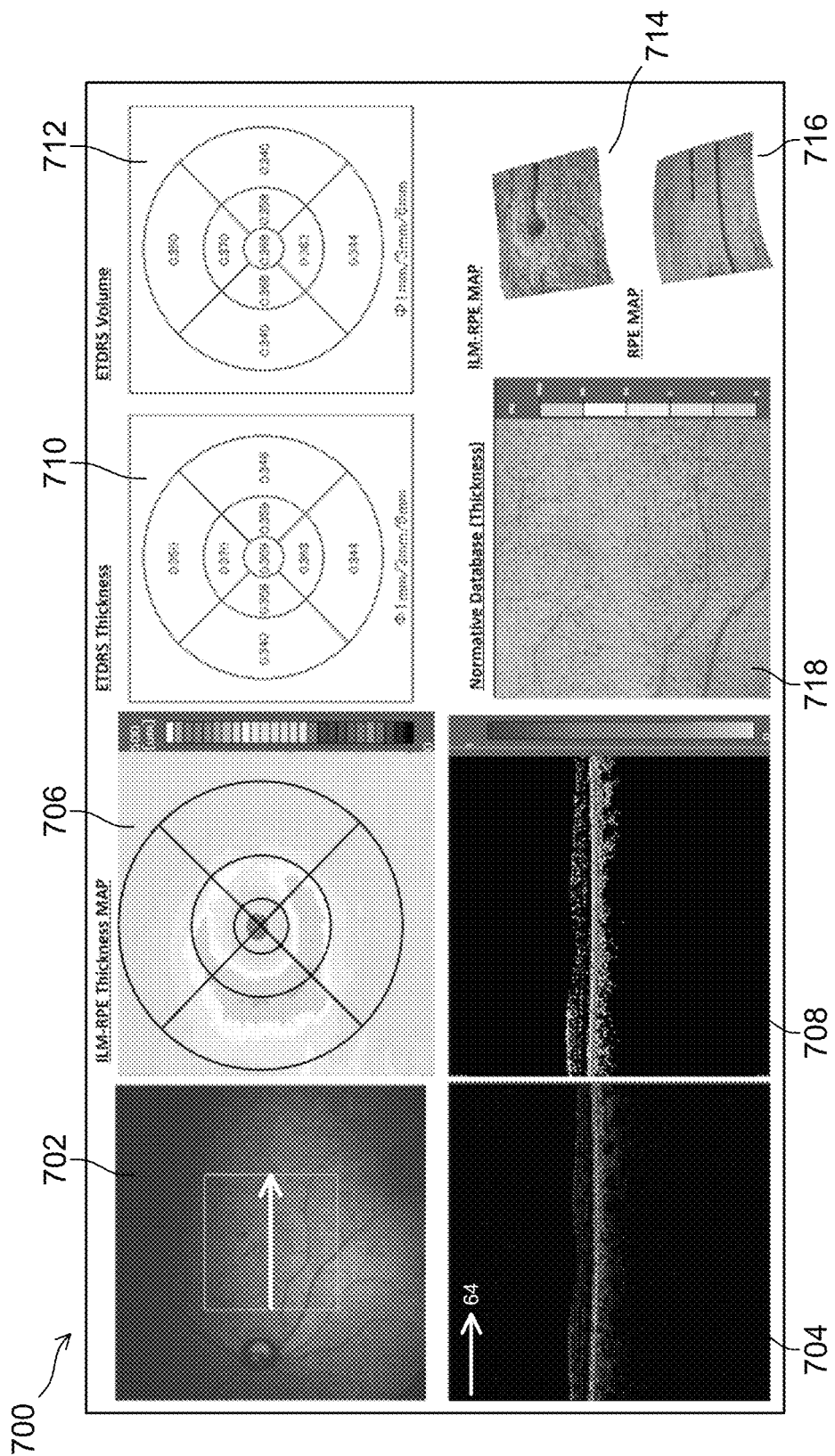
FIG. 8 illustrates an image indicating a macula map which is another example of the examination report(s).

FIG. 8 is an example of display images 700 of the macula map. The macula map is generated by analyzing the captured data captured in the capturing step set as the "Cube". As illustrated in FIG. 8, the macula map includes a fundus image 702, a tomographic image 704, an en-face image 706 indicating thickness, a tomographic image 708 indicating entropy, and maps 710 and 712 indicating quantitative evaluations of an average value of thickness and volume, respectively, and maps 714 and 716 indicating the surface of the subject eye 500. Each of the tomographic images 704 and 708 shows a cross-section at a position indicated by the arrow in the fundus image 702. The en-face e image 706 indicates an area surrounded by the square in the fundus image 702. Each of the maps 710, 712 indicating quantitative evaluations corresponds to circles and lines shown in the en-face images 706 indicating thickness. The macula map also includes an en-face images 718 indicating thickness of the normal eye. As described above, by virtue of the macula map including various images relating to the macule which can be generated from the captured data captured in the "Cube", it becomes easier to grasp the state of the macule of the subject eye 500.

Figure 9:
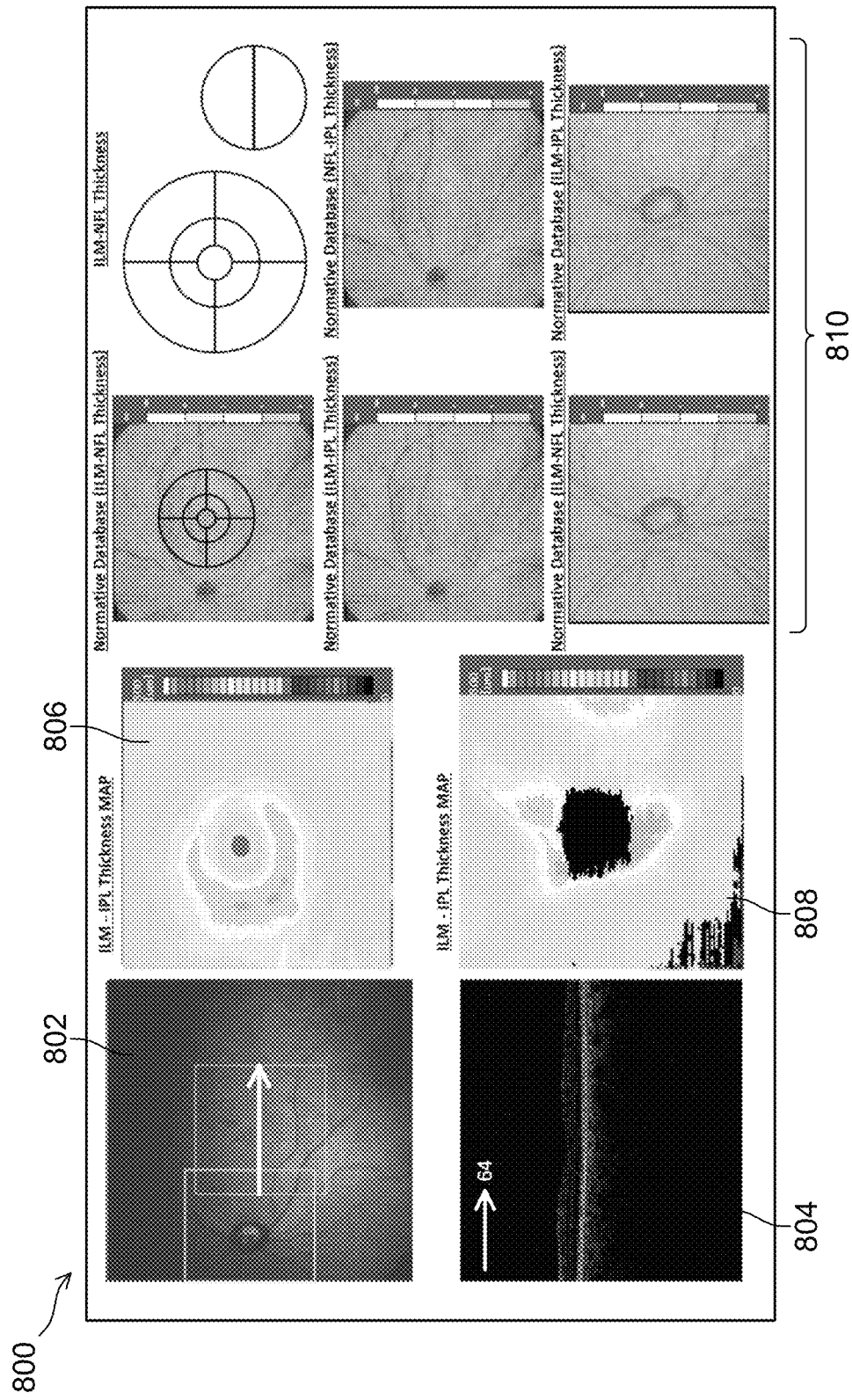
FIG. 9 illustrates an image indicating a glaucoma map which is another example of the examination report(s).

FIG. 9 is an example of display images 800 of the glaucoma map. The glaucoma map is generated by analyzing two pieces of captured data captured in the capturing steps set as "Cube" and "Cube Disk". As illustrated in FIG. 9, the glaucoma map includes a fundus image 802, a tomographic image 804, and en-face images 806 and 808 indicating thickness of the subject eye 500. The tomographic image 804 shows a cross section at a position indicated by the arrow in the fundus image 802. The en-face image 806 shows a region surrounded by the right square in the fundus image 802 (a region including the macula), and the en-face image 808 shows a region surrounded by the left square in the fundus image 802 (a region including an optic nerve head). The tomographic image 804 and the en-face image 806 are generated from the captured data captured in the "Cube", and the en-face image 808 is generated from the captured data captured in the "Cube Disk". The glaucoma map also includes a plurality of en-face images 810 each indicating thickness of the normal eye. Each of the plurality of en-face images 810 is an en-face image of the normal eye in various depthwise ranges, and is generated from the captured data obtained by capturing the normal eye in each of the "Cube" and "Cube Disk". As described above, by virtue of the glaucoma map including the various images relating to glaucoma which can be generated from the captured data captured in the "Cube" and the "Cube Disk", it becomes easier to grasp the disease state relating to the glaucoma of the subject eye 500.

Second Embodiment

In the first embodiment described above, the intended examination report type(s) is selected from the plurality of examination report types, and capturing of the subject eye 500 is performed so that the examination report(s) of the selected examination report types can be generated, but such a configuration is not limiting. For example, the subject eye 500 may be captured according to a capturing program capable of generating examination reports of all of the plurality of examination report types that can be selected. The present embodiment is different from the first embodiment in that the memory 204 is configured to store one capturing program including capturing steps capable of generating all of the examination reports of all the plurality of examination report types, and the rest of its configurations is the same as the first embodiment. Therefore, the description of the same configuration as that of the first embodiment is omitted.

Figure 10:
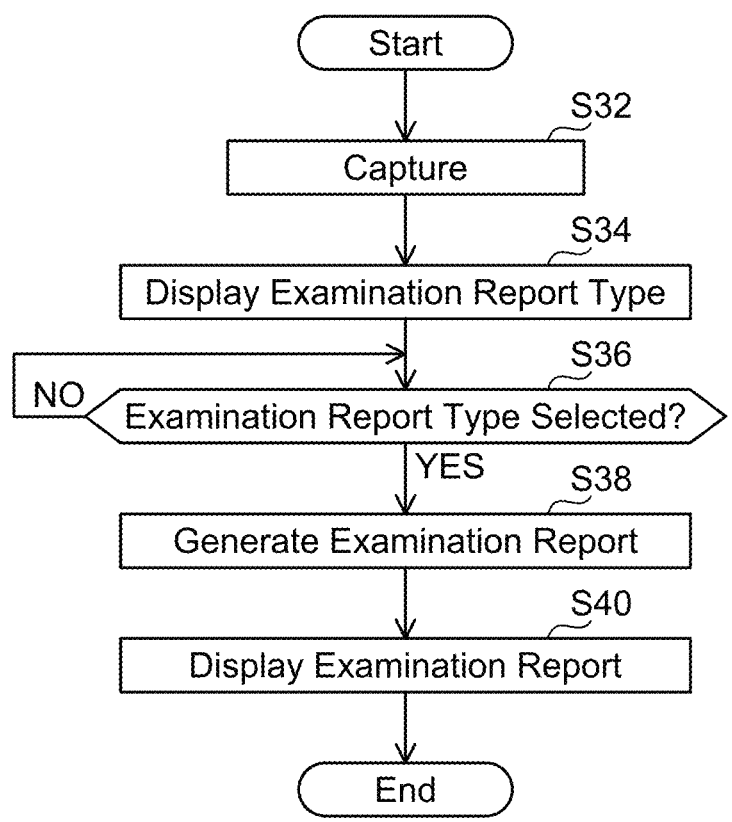
FIG. 10 is a flowchart illustrating an example of a process for generating examination report(s) in the second embodiment.

FIG. 10 is a flowchart illustrating an example of a process of generating examination report(s) of the subject eye 500 in the present embodiment. As illustrated in FIG. 10, the processor 202 at first performs capturing of the subject eye 500 in accordance with the capturing program stored in the memory 204 (S32). In the first embodiment described above, the capturing program is generated in accordance with the selected examination report type(s), and the capturing of the subject eye 500 is executed in accordance with the generated capturing program. In the present embodiment, however, the capturing of the subject eye 500 is performed in accordance with the preset capturing program.

For example, in the present embodiment, it is assumed that three examination reports of the "Polarization Map", "Macula Map" and "Glaucoma Map" can be generated. As described above, the capturing step for generating the "Polarization Map" is "Cube", the capturing step for generating the "Macula Map" is "Cube", and the capturing steps for generating the "Glaucoma Map" are "Cube" and "Cube Disk" (see FIG. 6). Therefore, the capturing program capable of generating the three examination reports of "Polarization Map", "Macula Map" and "Glaucoma Map" is set to include "Cube" and "Cube Disk". Therefore, the processor 202 performs the two capturing steps of the "Cube" and "Cube Disk" according to the capturing program. The captured data captured in each of the capturing steps is stored in the memory 204.

Next, as illustrated in FIG. 10, the processor 202 causes the monitor 120 to display the examination report types that can be generated (S34). For example, in the example described above, the three examination reports that can be generated are the "Polarization Map", "Macula Map" and "Glaucoma Map". In this case, the processor 202 displays the three examination report types of the "Polarization Map", "Macula Map", and "Glaucoma Map" on the monitor 120.

Next, it is determined whether one or a plurality of examination report types have been selected (S36). The process of step S36 is the same as the process of step S14 of the first embodiment, and therefore a detailed description thereof is omitted.

When the one or plurality of examination report types are selected, the processor 202 generates the examination report(s) corresponding to the examination report type(s) selected in step S36 (S38). At this time, among a group of the captured data stored in the memory 204, captured data captured in the capturing step(s) corresponding to the selected examination report type(s) is used. For example, when the "Polarization Map" and "Macula Map" are selected in step S36, the processor 202 generates the "Polarization Map" and the "Macula Map" using the captured data captured in the "Cube". Thereafter, the processor 202 displays the examination report(s) generated in step S38 on the monitor 120 (S40).

In the above-described examples, since the examiner selects the "Polarization Map" and "Macula Map" even though the two capturing steps of "Cube" and "Cube Disk" are performed according to the preset capturing program, only the captured data captured in the "Cube" is used, and the captured data captured in the "Cube Disk" is not used. However, when the examiner intends to generate the "Glaucoma Map" after the capturing, the "Glaucoma Map" can be generated using the captured data captured in the "Cube Disk" among the already captured data. Therefore, while a single capturing time may be longer, examination report(s) that is different from the examination report(s) intended at the time of capturing can be generated without recapturing. There may be a case where other examination report(s) may be needed as a result of evaluation on the examination report(s) intended at the time of capturing. In such a case, other examination report(s) can be generated without recapturing, and burden on an examinee and an examiner can be reduced.

In the above embodiments, the polarization-sensitive optical coherence tomographic device is used, but such a configuration is not limiting. A type of optical interference tomography is not particularly limited, and it may for example be an optical coherence tomographic device that is not polarization-sensitive. Further, in the second embodiment, the examination report type(s) of the examination report(s) to be outputted is selected after the capturing, but the capturing may be started after the examination report type(s) is selected as with the first embodiment.

Specific examples of the disclosure herein have been described in detail, however, these are mere exemplary indications and thus do not limit the scope of the claims. The art described in the claims includes modifications and variations of the specific examples presented above. Technical features described in the description and the drawings may technically be useful alone or in various combinations, and are not limited to the combinations as originally claimed. Further, the purpose of the examples illustrated by the present description or drawings is to satisfy multiple objectives simultaneously, and satisfying any one of those objectives gives technical utility to the present disclosure.

What is claimed is:

1. An optical coherence tomographic device comprising:
an image capturing unit configured to capture a tomographic image of a subject eye by performing a predetermined scan for scanning light entered in the subject eye;
an input device configured to input one or a plurality of examination report types, each of the examination report types indicating an intended examination report form;
a memory configured to store a plurality of capturing conditions, wherein each of the plurality of capturing conditions is a condition for performing a scan; and
a controller configured to control the image capturing unit, when the plurality of examination report types is inputted, according to a series of capturing conditions set based on corresponding ones of capturing conditions stored in the memory,
wherein the examination report type comprises a first examination report type indicating a first examination report form and a second examination report type indicating a second examination report form,
a first capturing condition corresponding to the first examination report type includes a specific capturing condition,
a second capturing condition corresponding to the second examination report type includes the specific capturing condition, and
when the first examination report type and the second examination report type are inputted by the input device, the controller is configured to set the series of capturing conditions by omitting the specific capturing condition comprised in one of the first capturing condition and the second capturing condition.

2. The optical coherence tomographic device according to claim 1, wherein
for each of the examination report types, the controller is configured to generate an examination report of the examination report type based on captured data captured by performing a scan according to the capturing condition corresponding to the examination report type among a group of captured data obtained by performing the scan according to the series of capturing conditions.

3. The optical coherence tomographic device according to claim 1, further comprising an output device configured to output examination reports of the plurality of examination report types generated from captured data captured according to the series of capturing conditions.

4. An optical coherence tomographic device comprising:
an image capturing unit configured to capture a tomographic image of a subject eye by performing a predetermined scan for scanning light entered in the subject eye;
a memory configured to store capturing conditions for causing the image capturing unit to perform capturing from which examination reports of a plurality of examination report types are able to be generated;
a controller configured to cause the image capturing unit to perform the capturing according to the capturing conditions stored in the memory;
an input device configured to input a capturing instruction to the image capturing unit and input at least one type of the plurality of examination report types; and
a generator configured to generate at least one of the examination reports corresponding to the at least one type inputted by the input device based on specific capturing data comprised in a group of captured data obtained by the controller causing the image capturing unit to perform the capturing according to the capturing conditions,
wherein the capturing conditions comprise a series of capturing conditions having a plurality of capturing conditions capable of generating the examination reports corresponding to the plurality of examination report types,
when the capturing instruction is inputted to the input device, the controller causes the image capturing unit to perform the capturing according to the series of capturing conditions,
each of the plurality of capturing conditions is a condition for performing a scan,
the plurality of examination report types comprises a first examination report type indicating a first examination report form and a second examination report type indicating a second examination report form,
a first capturing condition corresponding to the first examination report type includes a specific capturing condition,
a second capturing condition corresponding to the second examination report type includes the specific capturing condition,
in the series of capturing conditions, the specific capturing condition comprised in one of the first capturing condition and the second capturing condition is omitted, and
the generator generates the at least one of the examination reports corresponding to the at least one type inputted by the input device based on the specific capturing data comprised in a group of captured data obtained by the controller causing the image capturing unit to perform the capturing according to the series of capturing conditions.

* * * * *